(12) United States Patent
Rose

(10) Patent No.: US 7,364,583 B2
(45) Date of Patent: Apr. 29, 2008

(54) HEAD MOUNTED PHOTOEFFECTIVE DEVICE

(75) Inventor: Robert J Rose, Fryeburg, ME (US)

(73) Assignee: Physician Engineered Products Inc., Fryeburg, ME (US)

( * ) Notice: Subject to any disclaimer, the term of this patent is extended or adjusted under 35 U.S.C. 154(b) by 151 days.

(21) Appl. No.: 11/091,123

(22) Filed: Mar. 28, 2005

(65) Prior Publication Data

US 2005/0237479 A1    Oct. 27, 2005

Related U.S. Application Data

(60) Provisional application No. 60/565,109, filed on Apr. 23, 2004.

(51) Int. Cl.
*A61N 5/06* (2006.01)

(52) U.S. Cl. ........................................ 607/88

(58) Field of Classification Search ............ 607/88–92; 351/200, 203
See application file for complete search history.

(56) References Cited

U.S. PATENT DOCUMENTS

| | | | |
|---|---|---|---|
| 4,660,723 A | 4/1987 | Dechirot |
| 4,893,291 A | 1/1990 | Bick et al. |
| 5,008,865 A | 4/1991 | Shaffer et al. |
| 5,083,858 A | 1/1992 | Girerd |
| 5,140,562 A | 8/1992 | Moore-Ede et al. |
| 5,163,426 A | 11/1992 | Czeisler et al. |
| 5,167,228 A | 12/1992 | Czeisler et al. |
| 5,176,133 A | 1/1993 | Czeisler et al. |
| 5,197,941 A | 3/1993 | Whitaker |
| 5,242,941 A | 9/1993 | Lewy et al. |
| 5,243,568 A | 9/1993 | Burch et al. |
| 5,304,212 A | 4/1994 | Czeisler et al. |
| 5,420,152 A | 5/1995 | Lewy et al. |
| 5,447,527 A | 9/1995 | Waldman |
| 5,447,528 A | 9/1995 | Gerardo |
| 5,503,637 A | 4/1996 | Kyricos et al. |
| 5,545,192 A | 8/1996 | Czeisler et al. |

(Continued)

FOREIGN PATENT DOCUMENTS

WO    WO 91/14475    10/1991

(Continued)

OTHER PUBLICATIONS

"Bright Light Treatment", 2002, [online] [retrieved on Sep. 16, 2003] Retrieved from the Internet <URL:http//www.sunbox.com/Research/—Bright Light Treatment- The Sun Box Company—A L, pp. 1-5, The Sun Box Company.

(Continued)

*Primary Examiner*—Roy D. Gibson
(74) *Attorney, Agent, or Firm*—Vern Maine & Associates

(57) ABSTRACT

A system for exposure of eyes of a user to light is disclosed. That system comprises: a head mountable housing and at least one array of light emitting diodes disposed within the housing proximate to the eyes, and whereby light emissions are transmitted to the eyes. A controller is coupled to the light emitting diodes, and controls the intensity, duration, and sequences of the light emissions. Also provided is portable electrical charge storage cell, disposed within the housing, whereby an electrical current is supplied to the at least one array of light emitting devices.

16 Claims, 5 Drawing Sheets

U.S. PATENT DOCUMENTS

| | | | |
|---|---|---|---|
| 5,589,741 A | 12/1996 | Terman et al. | |
| 5,591,768 A | 1/1997 | Lewy et al. | |
| 5,641,801 A | 6/1997 | Wurtman | |
| 5,648,656 A | 7/1997 | Begemann et al. | |
| 5,707,652 A | 1/1998 | Lewy et al. | |
| 5,709,645 A * | 1/1998 | Siever | 600/27 |
| 5,805,267 A * | 9/1998 | Goldman | 351/203 |
| 5,824,024 A | 10/1998 | Dial | |
| 5,919,217 A | 7/1999 | Hughes | |
| 5,923,398 A | 7/1999 | Goldman | |
| 6,053,936 A | 4/2000 | Koyama et al. | |
| 6,158,884 A * | 12/2000 | Lebby et al. | 368/282 |
| 6,164,787 A | 12/2000 | Seki et al. | |
| 6,235,046 B1 | 5/2001 | Gerdt | |
| 6,350,275 B1 | 2/2002 | Vreman et al. | |
| 6,403,651 B1 | 6/2002 | Kennaway | |
| 6,464,715 B1 | 10/2002 | Gysens et al. | |
| 6,488,698 B1 | 12/2002 | Hyman | |
| 6,554,439 B1 | 4/2003 | Teicher et al. | |

FOREIGN PATENT DOCUMENTS

| | | |
|---|---|---|
| WO | WO 96/16697 | 6/1996 |

OTHER PUBLICATIONS

"White LED Step-Up Converter in SOT23", Catalog, 2002, pp. 1-9, 19-2028; Rev 1; Sep. 2002, Maxium Integrated Products, Sunnyvale, CA.

"LM431 Adjustable Precision Zener Shunt Regulator", Mar. 2002, pp. 1-12, National Semiconductor Corporation.

PCT Search Report dated Nov. 29, 2006 of Patent Application No. PCT/US05/10281 filed Mar. 28, 2005.

* cited by examiner

HEAD MOUNTED PHOTOEFFECTIVE DEVICE

RELATED APPLICATIONS

This application claims the benefit of U.S. Provisional Application No. 60/565,109, filed Apr. 23, 2004. This application is herein incorporated in its entirety by reference.

FIELD OF THE INVENTION

This invention relates to devices for the treatment of seasonal affective disorder or winter blues or for circadian rhythm adjustment; and more particular to photo-effective devices mounted on the users' head.

BACKGROUND OF THE INVENTION

Research has demonstrated that bright light—particularly blue to green visual range light (480 to 520 nanometers)—shone into the eyes of people will temporarily suppress brain melatonin levels and enhance brain serotonin—resulting in mood elevation for some and wakefulness. Subsequently, for a number of years, bright light shone into the eyes of subjects has been used to elevate the mood of people suffering from winter blues (or in more severe cases, seasonal affective disorder or S.A.D.), or to effect a change of one's circadian rhythm for the purpose of: avoiding jet lag fatigue, easing the transition for shift-change workers, and resetting the circadian clocks of those with delayed sleep phase syndrome, wherein people may lose their solar cues to their circadian rhythms and their wake-sleep cycles gradually become "out of sync" with day-night cycles. Other possible uses of bright light presently being researched include: treatments for premenstrual syndrome, certain sexual dysfunctions, antepartum depression, postpartum depression, other depression conditions, chronic fatigue syndrome, and wakefulness for commercial drivers, military personnel and astronauts. The means for delivering this bright light have included desktop devices, lights mounted on glasses frames, and the brightening of living quarters. Desktop devices require the user to sit in one place for approximately one-half hour per day. Since many people cannot find the time to sit in one place that long each day, compliance suffers. Presently available devices mounted on the frames of eyeglasses allow the user a higher degree of mobility, but are typically heavy and bulky to use. Techniques involving the brightening of entire living quarters are often prohibitively expensive for most users. In addition to the expense involved, the user is "confined to quarters" for a prescribed period each day. Such an inconvenience results in the same poor compliance as seen with desktop devices. In fact, cost has been a barrier for many would be users of known approaches.

What is needed, therefore, are techniques for treating individuals with controlled, high-intensity intensity blue-green light, with a portable device.

BRIEF SUMMARY OF THE INVENTION

One embodiment of the present invention provides a system for exposure of eyes of a user to light. That system comprises: a visor mountable housing and at least one array of light emitting devices disposed within the housing proximate to the eyes, and whereby light emissions are transmitted to the eyes. A controller is coupled to the light emitting devices, and controls the intensity, duration, and sequences of the light emissions. Also provided is portable electrical charge storage cell, disposed within the housing, whereby an electrical current is supplied to the at least one array of light emitting devices.

Another embodiment of the present invention provides such a system wherein the light emissions have wavelengths between 480 and 520 nanometers.

A further embodiment of the present invention provides such a system wherein the cell comprises a lithium polymer cell.

Still another embodiment of the present invention provides such a system further comprising an ambient light sensor coupled to the controller.

A still further embodiment of the present invention provides such a system wherein the controller is configured to adjust the intensity of the light emissions based upon data from the ambient light sensor.

Yet another embodiment of the present invention provides such a system wherein the array is a plurality of light emitting devices disposed along a line or otherwise disposed so as to produce a beam with a width adequate to accommodate various inter eyeball distances.

A yet further embodiment of the present invention provides such a system comprising at least one lens disposed within the housing between the at least one array of light emitting devices and the eyes. According to one such embodiment, the lens is frosted, thereby providing a diffuse light with no "hot spots".

Even another embodiment of the present invention provides such a system wherein the light emissions are directed by shields, disposed in the housing, to a region of the face of the subject encompassing the eyes. The term "shields" being used to refer not only to light blocking means but also light reflecting means.

An even further embodiment of the present invention provides such a system wherein the light emissions are substantially uniformly distributed over that region of the subject's face.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION OF THE INVENTION

One embodiment of the present invention provides for a relatively small, light-weight, highly portable, head-mounted device that provides high-intensity blue to green light, substantially over 2000 lux, into the eyes of the user. The light source array is configured within the device to provide an oval beam to each of the eyes to accommodate varying eye-to-eye distances among various users.

One embodiment of the present invention provides a device that is head-mounted to be situated in front of the user's eyes, but lies outside the visual axis of the user so the user can perform many normal daily activities that require vision. It may be removably or temporarily attached to the underside of a hat or visor brim for convenience and ease of use. In such an embodiment, the user aims the light at his/her eyes by tilting the visor up or down as needed. The user controls the device with a simple on/off switch. An automatic shut-off occurs after 30 minutes of use. The light source is powered by a rechargeable electrical power source within the device.

In one embodiment, the light is directly focused into the eye of the user. In some instances, users may be instructed periodically look in to the light, exposing the fovea of the eye to the light. Such direct and intense exposure may optimize the benefits of the device. The light beam, according to one embodiment of the present invention, is focused on a region broad enough to accommodate various users having widely differing inter-eyeball distances. Other embodiments may include adjustable lateral aiming means.

Figure 1A:
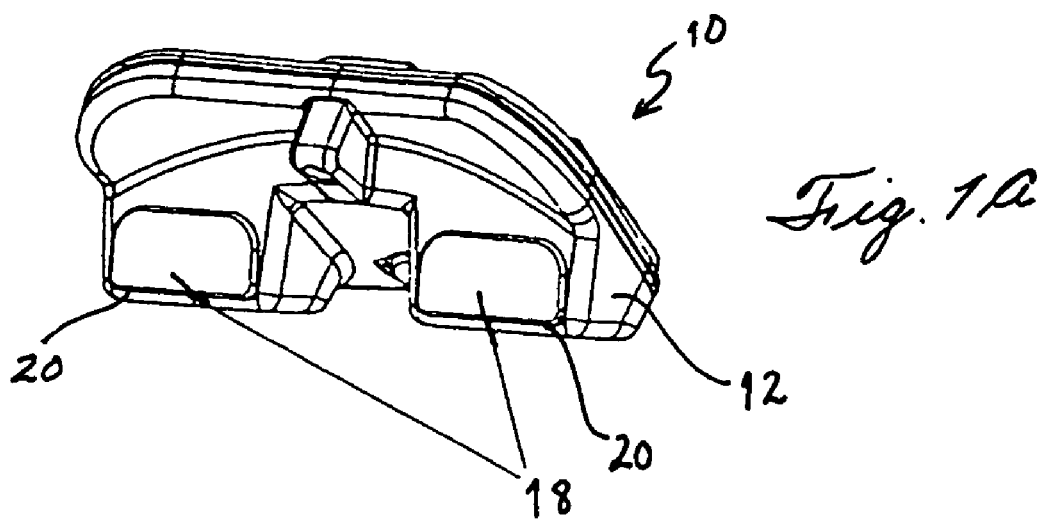
FIG. 1A is a perspective view illustrating the underside of a photo-therapeutic device configured in accordance with one embodiment of the present invention.
Figure 1B:
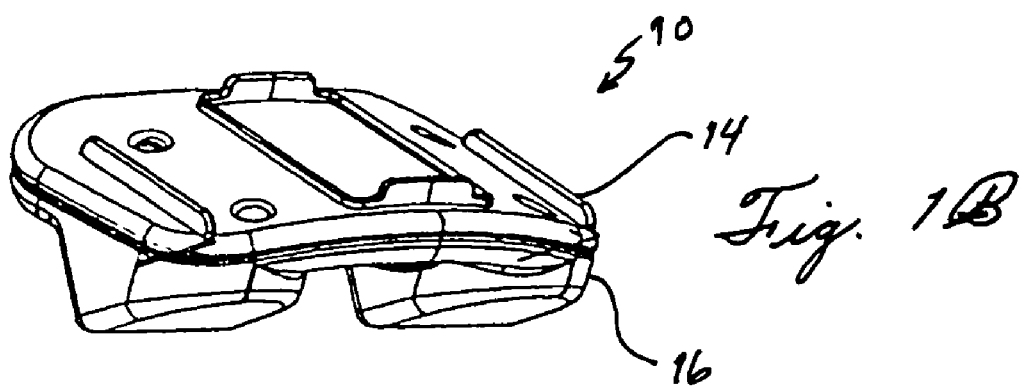
FIG. 1B is a perspective view illustrating the topside of a photo-therapeutic device configured in accordance with one embodiment of the present invention.
Figure 1C:
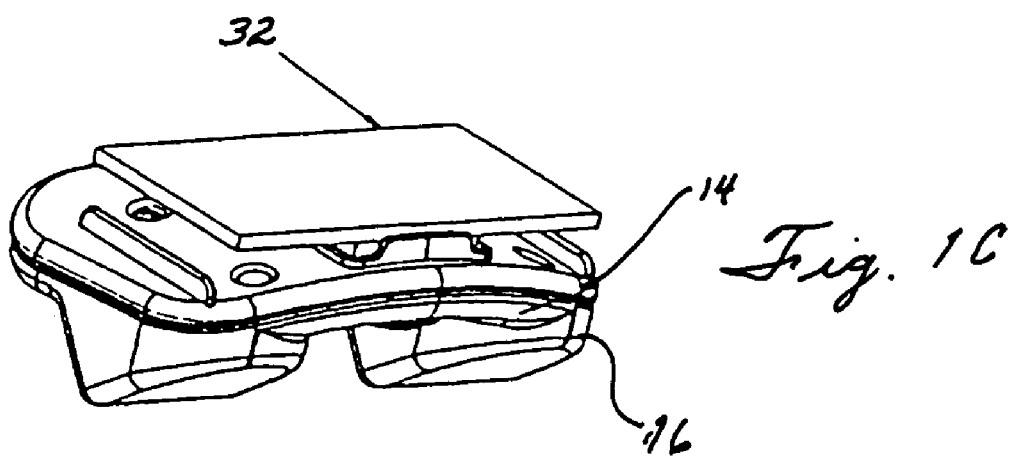
FIG. 1C is a perspective view illustrating the a photo-therapeutic device having a hat brim mounting device attached thereto and configured in accordance with one embodiment of the present invention.
Figure 2:
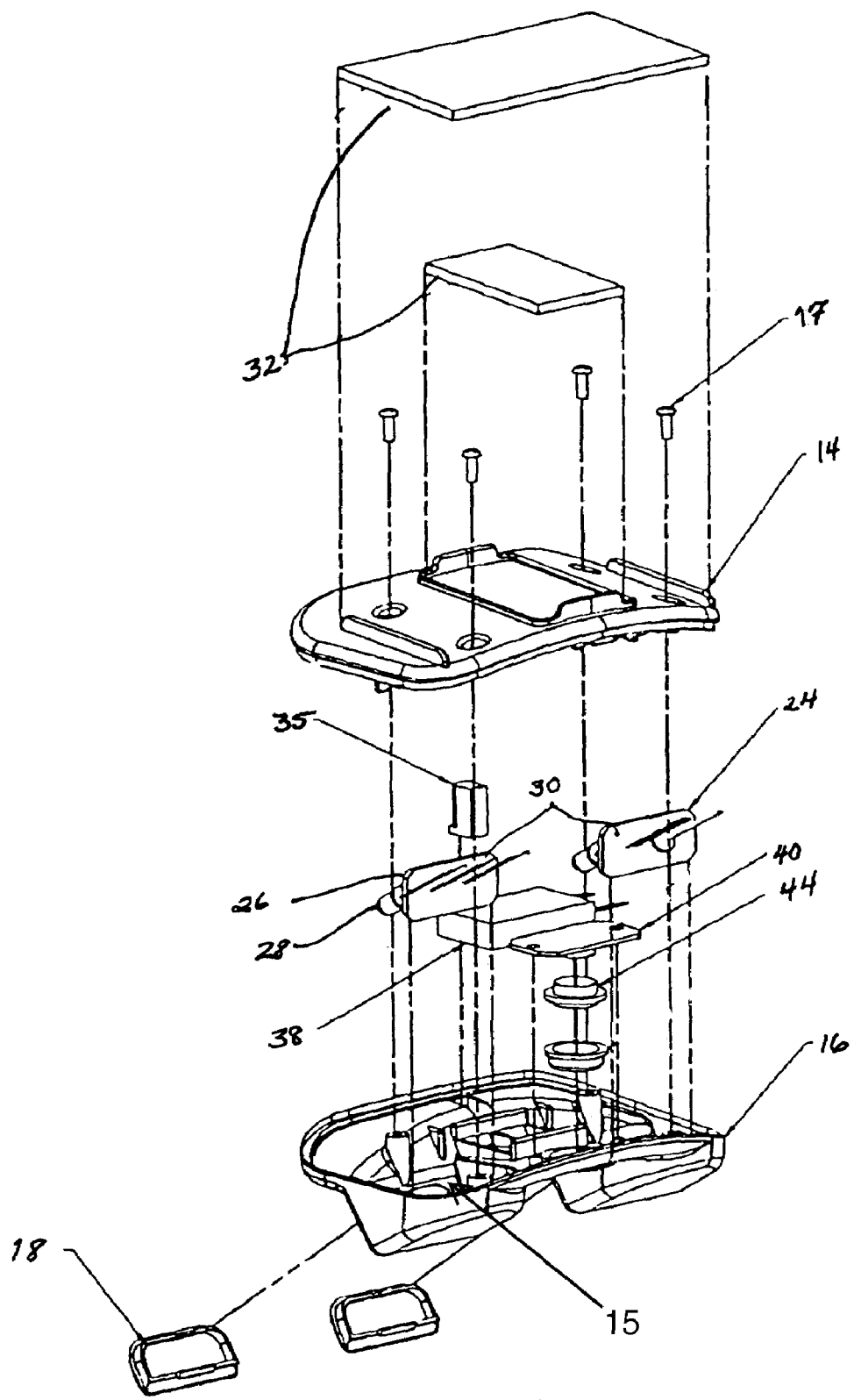
FIG. 2 is an exploded perspective view illustrating a photo-therapeutic device configured in accordance with one embodiment of the present invention.

According to one embodiment of the present invention, illustrated in FIG. 1A-1C, a visor mounted photo-effective device 10 is provided, having a housing 12. The housing 12 may comprise top 14 and bottom 16 housing pieces. Mounted within windows or apertures 20 in the housing 12 are first and second lenses 18. The lenses are secured to the housing 12 at a joint 20. As illustrated in FIG. 2, Disposed within the housing 12 are first and second arrays of lights 24,26. These arrays of lights 24,26, according to one embodiment may be at least one light emitting diode (LEDs) or other light emitting device 28, and in some embodiments, more specifically light emitting devices emitting light having a wavelength of between about approximately 480 to 520 nanometers (nm). Such light arrays are controlled by circuitry disposed on a printed circuit board 30. A mounting structure 32 is mounted on the housing 12 facilitating the adhesion or mounting of the phototherapeutic device on the underside of a visor or hat brim (not shown). Shields 15 are also provided to direct the light towards theh eyes of the user and are disposed in the housing 12.

Figure 3:
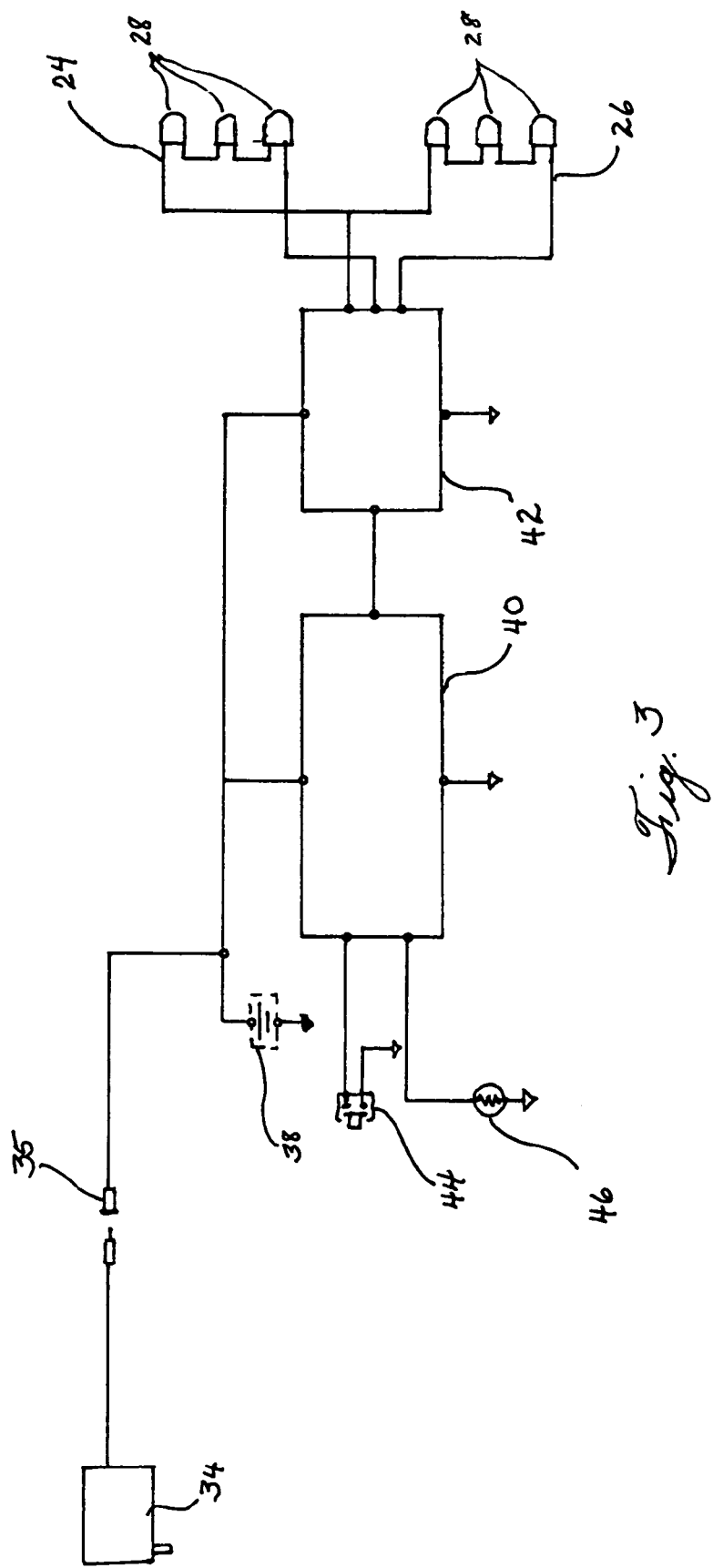
FIG. 3 is a block diagram illustrating the circuitry of a photo-therapeutic device configured in accordance with one embodiment of the present invention.

According to one embodiment, the circuitry disposed on the printed circuit board 30, such as in one embodiment of the present invention illustrated in FIG. 3, may comprise connections 35 to a charging adaptor 34, and to the power source 38. A micro-controller 40 regulates the maximum time of treatment. The time setting may be programmed to a standard regime or may in some embodiments be programmed according to an individualized regimen. In one embodiment, the micro-controller 40 permits the light sources 24,26 to be illuminated for up to 30 minutes (1800 seconds)

According to one embodiment, illustrated in FIGS. 1A-1C and 2, the device is housed in molded plastic housing 12 having top 14 and bottom 16 housing pieces, measuring in one embodiment 2.394" long×3.780" wide×1.192" high. These pieces 14,16 are either attachable to each other with screws 17 or other reversible attaching mechanism, or permanently attached to each other by glue or heat-sealing. Embodiments where the housing pieces 14,16 are reversibly attached to each other allow for access to internal components for repair or replacement, and for quality-related internal device inspections. Whereas embodiments where the housing pieces 14,16 are permanently attached to each other minimize end-user manipulation and maximizes water-resistance.

According to one such an embodiment, two clear or frosted plastic lenses 18 insert into the two windows 20 on either side of the rear of the device housing 12, such that when in use the lenses 18 are disposed opposite to the users eyes. The housing 12 and the inserted lens pieces 18 may be coupled at a joint 22 having precise tolerances or with gasket material to provide for water resistance or waterproofing of the device.

The housing 12 is shaped to fit under standard billed hat or visor brims so that the top surface of the device nests against the curved under surface of the brim. 3-M Dual Lock material 32 or other similar re-usable adhesive material is attached to the top of the device and the bottom of the brim in such a pattern so as to dictate that the device is attached to the brim in a consistent position to ensure a consistent approximate 1-to-2-inch light-to-eye distance, and consistent center-line positioning so that each light array 24,26 mounted at each side of the device sits directly in front of each eye. In alternative embodiments, clips, clamps, hook and loop material and other mechanical fasteners may be used. In still other embodiments, the device may be permanently mounted to a dedicated visor or hat. Alternative embodiments may be mounted to the frames of eyeglasses or other head mounted frames. Still other alternative may have housings configured to be mounted beneath atypical hats or helmets, such as combat helmets.

According to one embodiment, the light source is an array 24,26 of high-intensity blue to green LED bulbs, e.g., Nichia America Corp Blue-Green LED Type NSPE590S, each with a 15 degree angle of beam, positioned inside the device, behind the plastic lenses 18, and positioned at a 30 degree downward angle as to aim at the user's eyes when attached to the underside of a billed hat or visor worn by the user, while the device 10 lies outside the visual axis of the user so the user can perform many normal daily activities while using the device.

According to one embodiment, and array of bulbs 24, 26, such as a 2- or 3-bulb array, is used on either side of the device—with the LED bulbs 28 set approximately ⅜" apart from each other in a horizontal configuration provides two oval beams of light of sufficient irradiance (approximately 10,000 to 16,000 lux) that are each approximately ¾ inches high and 1 inch wide at 2 inches distance from the light lens. This size and shape of light beam will accommodate the varying eye-to-eye distances among various users so that high-intensity light will strike the pupil of both eyes of almost any adult user.

According to one embodiment, the power source 38 used to power the LED lights 28 is an Ultralife lithium polymer battery, No. UBC641730, which provides 200 mAhr.—so as to run the 6 LED bulbs for ½ hour per day for 4 days at 10,000 lux or 2 days at 16,000 lux between recharges. Power sources of this type have a number of advantages for various embodiments of the present invention: such power supplies are light weight (4.5 gm.), have a long life, are rechargeable, and unlike nickel cadmium batteries, have the ability to maintain a full charge range regardless of the level of discharge prior to recharging. One skilled in the art will readily appreciate that other alternative embodiments may use other power sources.

As illustrated in FIG. 2, the two light source arrays 24,26 are each attached to a printed circuit board (PCB) 30. Each LED printed circuit board 30 fits into the side compartments of the device. These PCBs are wired to a centrally mounted PCB 40 with switch 44. Likewise, the centrally mounted battery 38 and recharging jack 35 are wired to the central PCB 40. The central PCB 40 contains, in one embodiment, an automatic shut-off feature after 30 minutes of run time. The device can be also turned on or off at will by pushing the switch.

According to one embodiment, illustrated in FIG. 3, the unit 10 comprises four major subsystems: a high energy density lithium-polymer cell 38, a micro-controller 40 to time and control the light-treatment process, a LED-driver 42 boost converter to drive the LEDs with constant current, and six blue-green narrow-beam LEDs 28, disposed in first and second arrays 24, 26 to provide the light. In alternative embodiments, the microcontroller 40 and driver 42, may be mounted on a single PCB. Likewise, alternative light emitting devices may be used, such as polymer light emitting diodes, and other suitable light sources A high energy density lithium-polymer cell 38 providing a lightweight power source allowing the unit to be easily supported up under the visor of a billed cap, such as those commonly referred to as "baseball caps". The cell contains no metallic lithium, no liquid electrolyte, and features a protection module that limits discharge rate and precludes over and undercharging to ensure user safety. The cell 38 is rechargeable via a charging adaptor 34.

According to one embodiment a micro-controller 40 controls the light treatment process. It provides a 30-minute timed exposure to optimize the treatment efficiency. The intensity of the LED 28 is settable at 2 levels via an intensity control switch 44 and the LED INTENSITY CONTROL input to the LED DRIVER controller 42 described below. One embodiment includes a photo-sensor 46 to sense ambient light level. The controller 40, according to one embodiment, automatically adjusts LED intensity depending on the input from the photo-sensor 46, thereby minimizing any glare effect at low ambient light levels and increasing intensity to higher levels in a bright environment. In one such embodiment, an electric eye 70 monitors light room light, and selects a light strength dependant upon ambient light conditions; ambient light 100-1000 lux may convert to 8,000 lux of in-eye light; 1000-3000 lux converts to 9000 lux; 3000-8000 lux: 10,000 lux; 8000-20,000 lux: 11,000 lux; 20000-40000 lux: 12,000 lux. Such a schema covers the commonly experienced wide range of ambient light (100 lux-40,000 lux) and relates to stepped doses in the acceptable therapeutic range (8,000-12,000 lux). There may be many other similar configurations. The more the in-eye intensity exceeds the ambient intensity, the more glare effect you get. So, a dim room of 100-400 lux gets the minimal 8000 lux dose, but a 7000-7900 lux difference. A 1000-3000 lux ambient gets 9000 lux=a 6000-8000 lux difference. 3000-8000 ambient results in 10000 lux=a 2000-7000 lux differenc. 8000-20000 ambient gets 11,000 lux=a 2000 to −9000 lux difference. 20000 to 40000 lux gets 12,000 lux=a −8000 to −28,000; lux difference. One skilled in the art will readily appreciate that a difference may be empirically determined that affords maximum therapeutic effect, while minimizing glare. In some embodiments, the electric eye may be ⅛-¼" in diameter and mounted on the front, center edge of the housing and disposed facing away from the eyes to sense the room light condition.

The LED driver circuit 42 boosts the 3.7V nominal voltage available at the cell terminals 38 up to a higher voltage suitable to drive 3 blue-green LEDs 28 in series. The circuit regulates the current through the two LED strings to ensure constant LED color and intensity over the full cell discharge voltage range. LED current output is continuously adjustable from 5 mA to 50 mA via the circuit's LED INTENSITY CONTROL input.

Figure 5:
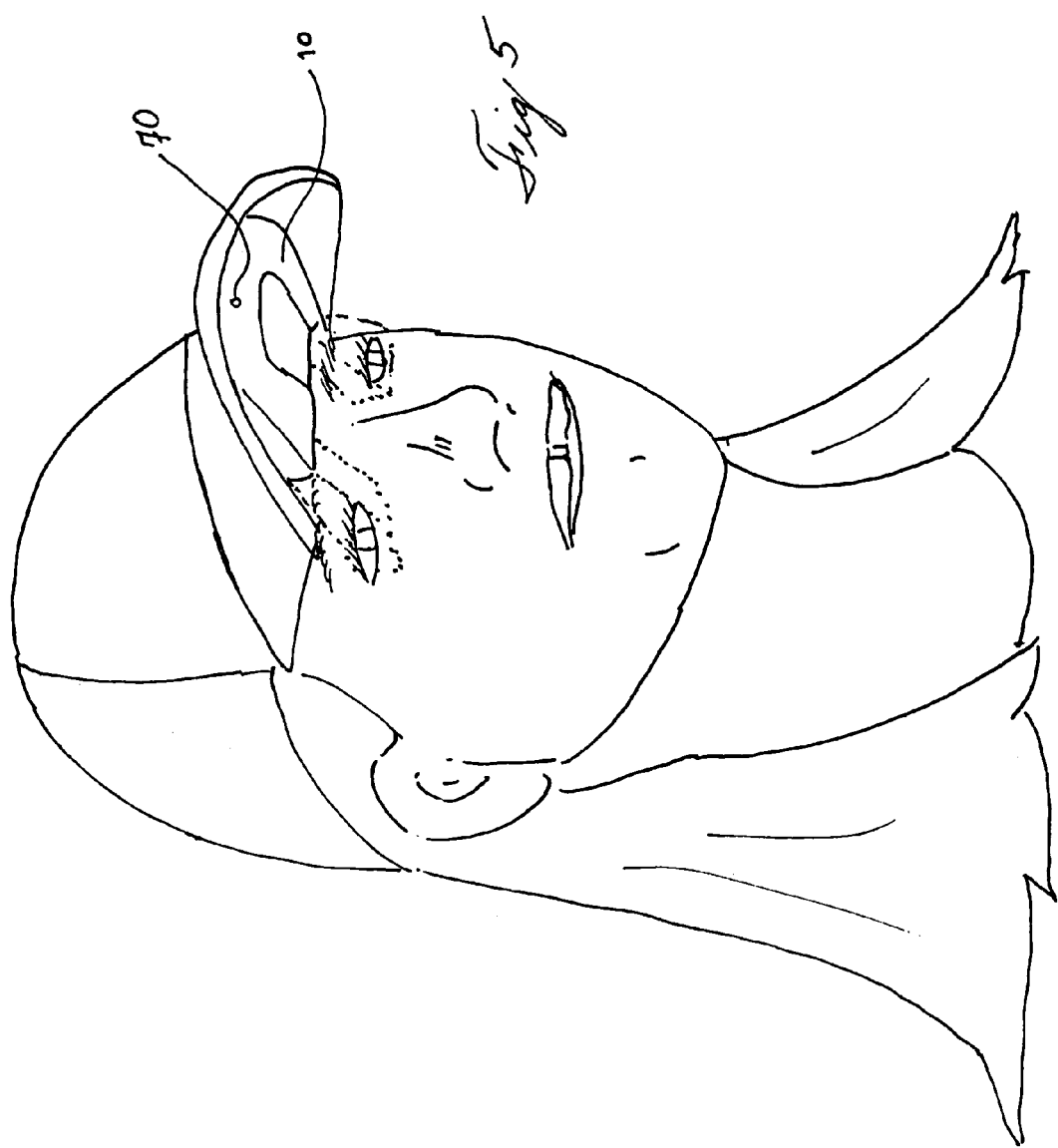
FIG. 5 is a perspective view of a user wearing a phototherapeutic device according to one embodiment of the present invention.

The 6 light-emitting diodes 28 output blue-green light at a wavelength peaking at about approximately 500 nm and a relatively narrow range of light spectrum deemed to be the optimum frequency to achieve the desired effect. The LED output is concentrated in a narrow beam maximizing the energy that can be directed down through the pupil and onto the retina. In one embodiment, illustrated in FIG. 5, treatment is applied for 30 minute intervals with an intensity of light between 10,000 and 16,000 lux. The device is disposed within 1 to 2 inches of the face slightly above the brow of the user.

Figure 4:
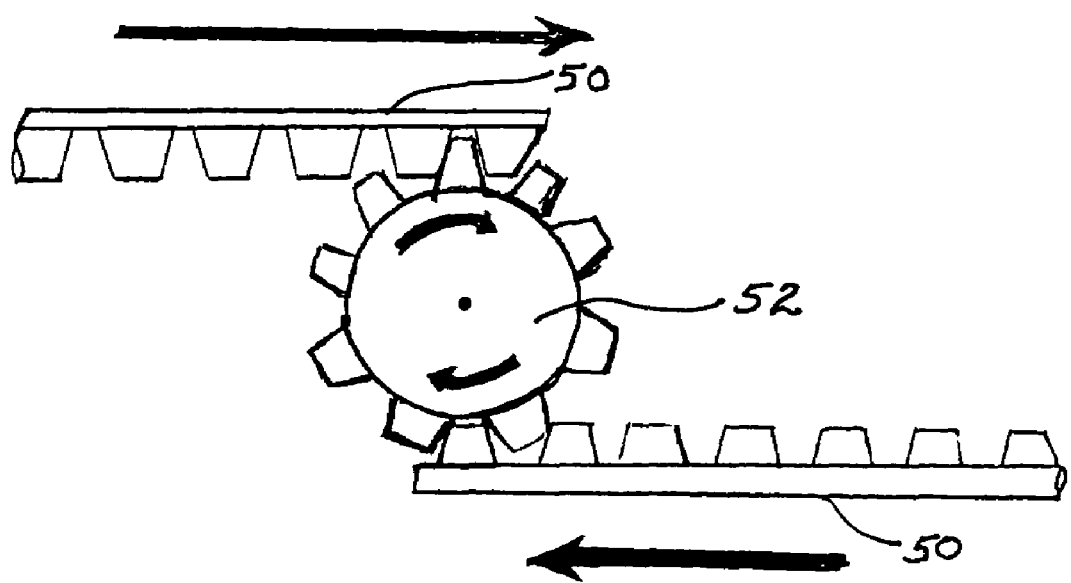
FIG. 4 is an elevation view of a interfoci adjustment configured according to one embodiment of the present invention.

In some embodiments, a rack and pinion system, such as illustrated in FIG. 4, may be provided, so as to permit the adjustment of the distance between foci of the light beams. The adjustment allows the user to configure the device for use by individuals having varying interocular distances. This adjustment may comprise opposing geared racks 50 configured to mate with a common gear or pinion 52. The pinion 52 may be manually or electronically manipulated. According to one embodiment, rotation of the pinion 52 in a clockwise orientation causes the racks 50 to slide inward, thereby decreasing the distance between light arrays 24, 26. Conversely, rotation in the opposite direction would increase the distance between the arrays 24, 26.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited neither by this detailed description nor by the exemplary claims appended hereto.

What is claimed is:

1. A system for exposure of eyes of a human subject to light, said system comprising:
   a head mountable housing;
   at least one array of light emitting devices disposed within said housing proximate to said eyes, and whereby light emissions are transmitted to said eyes;
   a controller coupled to said light emitting devices, whereby intensity, duration, and sequences of said light emissions are controlled;
   a portable electrical charge storage cell disposed within said housing and whereby an electrical current is supplied to said at least one array of said light emitting devices;
   an ambient light sensor coupled to said controller, said sensor being disposed on a side of said housing distal to said eyes such that said sensor measures ambient light; and wherein said light emissions are directed by shields, disposed in said housing, to a region of the face of said subject encompassing said eyes.

2. The system of claim 1 wherein said light emissions have wavelengths between about approximately 480 and 520 nanometers.

3. The system according to claim 2 wherein said light emissions have a peak wavelength of 500 nanometers.

4. The system according to claim 1 wherein said cell comprises a lithium polymer cell.

5. The system according to claim 1 wherein said controller is configured to adjust the intensity of said light emissions based upon data from said ambient light sensor.

6. The system according to claim 1 wherein said array is a plurality of said light emitting diodes disposed along a line.

7. The system according to claim 1 further comprising at least one lens disposed within said housing between said at least one array of light emitting diodes and said eyes.

8. The system according to claim 1 wherein said light emissions are substantially uniformly distributed over said region of face.

9. The system according to claim 1 wherein said region has adequate area to accommodate a variety of users having various inter-eyeball distances.

10. The system according to claim 1 wherein a distance between said light emissions may be adjusted.

11. The system according to claim 1 wherein said portable electrical charge storage cell is a battery.

12. An apparatus for photo-effective treatment of a subject, said apparatus comprising:

a casing;

first and second light emitting arrays;

a controller unit whereby the light emitted from the array is regulated;

a sensor whereby ambient light levels are measured, said sensor communicating with said controller unit;

a portable electrical charge storage cell disposed within said casing and whereby an electrical current is supplied to said first and second light emitting arrays; and an interfoci distance adjustment.

13. The apparatus of claim 12 wherein said first and second light emitting arrays comprise light emitting diodes configured to emit light having a wavelength between 480 and 520 nanometers.

14. The apparatus according to claim 12 wherein said cell comprises a lithium polymer cell.

15. The apparatus according to claim 12 wherein said interfoci distance adjustment comprises first and second racks disposed so as to move in opposing directions when actuated by a pinion disposed between said first and second racks.

16. The apparatus according to claim 12 further comprising a sliding track by which said arrays may be symmetrically repositioned.

* * * * *